United States Patent
Niwano et al.

(10) Patent No.: US 9,962,364 B2
(45) Date of Patent: May 8, 2018

(54) WOUND HEALING ACCELERATOR

(71) Applicant: A-Z LTD., Sendai-shi, Miyagi (JP)

(72) Inventors: Yoshimi Niwano, Osakasayama (JP); Taro Kanno, Sendai (JP); Keisuke Nakamura, Sendai (JP); Minoru Kanno, Sendai (JP)

(73) Assignee: A-Z LTD., Sendai (JP)

( * ) Notice: Subject to any disclaimer, the term of this patent is extended or adjusted under 35 U.S.C. 154(b) by 77 days.

(21) Appl. No.: 14/654,864

(22) PCT Filed: Dec. 25, 2013

(86) PCT No.: PCT/JP2013/084592
§ 371 (c)(1),
(2) Date: Jun. 23, 2015

(87) PCT Pub. No.: WO2014/104064
PCT Pub. Date: Jul. 3, 2014

(65) Prior Publication Data
US 2015/0335611 A1    Nov. 26, 2015

(30) Foreign Application Priority Data

Dec. 26, 2012   (JP) .................................. 2012-282607

(51) Int. Cl.
*A61K 31/353*  (2006.01)
*A61K 8/368*   (2006.01)
(Continued)

(52) U.S. Cl.
CPC .............. *A61K 31/353* (2013.01); *A23G 3/36* (2013.01); *A23G 4/06* (2013.01); *A23L 33/105* (2016.08); *A61K 8/347* (2013.01); *A61K 8/36* (2013.01); *A61K 8/368* (2013.01); *A61K 8/37* (2013.01); *A61K 8/498* (2013.01); *A61K 8/97* (2013.01);
(Continued)

(58) Field of Classification Search
CPC ..................................................... A61K 31/353
See application file for complete search history.

(56) References Cited

U.S. PATENT DOCUMENTS

| 4,873,227 A | 10/1989 | Ikada et al. |
| 2003/0133991 A1 | 7/2003 | Monroe et al. |

(Continued)

FOREIGN PATENT DOCUMENTS

| CA | 2 337 772 A1 | 1/2000 |
| FR | 5055 M | 5/1967 |

(Continued)

OTHER PUBLICATIONS

Aug. 10, 2016 Partial Search Report issued in European Patent Application No. 13867408.0.
(Continued)

*Primary Examiner* — Benjamin Packard
(74) *Attorney, Agent, or Firm* — Oliff PLC (57) ABSTRACT

The purpose of the present invention is to provide a specific wound healing accelerator effective for accelerating healing of wounds, particularly of wounds in the oral cavity, or a composition which includes the wound healing accelerator. This wound healing accelerator including a specific polyphenol is easy to handle and is capable of accelerating would healing even by contact for a short time.

6 Claims, 6 Drawing Sheets

(51) Int. Cl.
| | |
|---|---|
| A61K 8/49 | (2006.01) |
| A61K 31/192 | (2006.01) |
| A61K 31/216 | (2006.01) |
| A23G 3/36 | (2006.01) |
| A23G 4/06 | (2006.01) |
| A61K 8/36 | (2006.01) |
| A61K 8/37 | (2006.01) |
| A61Q 11/00 | (2006.01) |
| A61K 8/34 | (2006.01) |
| A61K 8/97 | (2017.01) |
| A23L 33/105 | (2016.01) |

(52) U.S. Cl.
CPC .......... *A61K 31/192* (2013.01); *A61K 31/216* (2013.01); *A61Q 11/00* (2013.01)

(56) References Cited

U.S. PATENT DOCUMENTS

| | | | |
|---|---|---|---|
| 2003/0203857 A1 | 10/2003 | Ohnogi et al. | |
| 2003/0203962 A1* | 10/2003 | Howell | A23L 2/02 514/456 |
| 2006/0165609 A1 | 7/2006 | Inaba et al. | |
| 2006/0293258 A1 | 12/2006 | Rohdewald | |
| 2007/0053851 A1 | 3/2007 | Maillan et al. | |
| 2009/0031691 A1 | 2/2009 | Tajima et al. | |
| 2009/0215884 A1 | 8/2009 | Ogbourne et al. | |
| 2010/0086542 A1 | 4/2010 | Castanas et al. | |
| 2010/0158885 A1 | 6/2010 | Huang et al. | |

FOREIGN PATENT DOCUMENTS

| | | |
|---|---|---|
| GB | 1130566 A | 10/1968 |
| JP | S63-107935 A | 5/1988 |
| JP | H03-77817 A | 4/1991 |
| JP | H03-106823 A | 5/1991 |
| JP | H05-117145 A | 5/1993 |
| JP | H06-336422 A | 12/1994 |
| JP | H09-124472 A | 5/1997 |
| JP | H10-45615 A | 2/1998 |
| JP | 2002-003353 A | 1/2002 |
| JP | 2002-053467 A | 2/2002 |
| JP | 2004-099527 A | 4/2004 |
| JP | 2004-217587 A | 8/2004 |
| JP | 2005-515191 A | 5/2005 |
| JP | 2005-213234 A | 8/2005 |
| JP | 2007-505064 A | 3/2007 |
| JP | 39-17370 B2 | 5/2007 |
| JP | 2008-543902 A | 12/2008 |
| JP | 2009-052185 A | 3/2009 |
| JP | 2009-517345 A | 4/2009 |
| JP | 2010-511026 A | 4/2010 |
| JP | 2012-519690 A | 8/2012 |
| MX | 2011005607 A | 12/2012 |
| WO | 01/76580 A1 | 10/2001 |
| WO | 20051092327 A1 | 10/2005 |
| WO | 2006136428 A2 | 12/2006 |
| WO | 20071010911 A1 | 1/2007 |
| WO | 2010099062 A1 | 9/2010 |
| WO | 2010101844 A1 | 9/2010 |
| WO | 2013/091140 A1 | 6/2013 |

OTHER PUBLICATIONS

Akkol et al: "Enhancement of wound healing by topical application of Scorzonera species: Determination of the constituents by HPLC with new validated reverse phase method," Journal of Ethnopharmacology, Elsevier Ireland, LTD, IE, vol. 137, No. 2., 2011, pp. 1018-1027.

Díaz-González, María et al. "Inhibition of deleterious chronic wound enzymes with plant polyphenols," Biocatalysis and Biotransformation, vol. 30, No. 1, 2012, pp. 102-110.

Viensah A Y et al: "Effects of Buddleja globosa leaf and its constituents relevant to wound healing," Medicinal & Aromatic Plants Abstracts, Scientific Publishers, Scientific Publishers, New Delhi, India, vol. 24, No. 2, Apr. 1, 2002.

Song, Ho Sun et al. "The Effect of Caffeic Acid on Wound Healing in Skin-incised Mice," Korean J Physiol Pharmacol, vol. 12, 343-437, Dec. 2008.

Nov. 18, 2016 Extended Search Report issued in European Patent Application No. 13867408.0.

Chen, WC. et al., "Effect of Topical Application of Chlorogenic Acid on Excision Wound Healing in Rats." Planta Med, vol. 79, pp. 616-621, 2013.

Watanabe, Eriko et al., "Coffee-san ni yoru Hito Hyohi Kakuka Saibo no Saibo Zoshoku Oyobi Bunka Sokushin Koka." Tiss. Cult. Res. Commun.,vol. 32, pp. 189-194, 2013.

Pastore, S. et al., "Plant Polyphenols Regulate Chemokine Expression and Tissue Repair in Human Keratinocytes Through Interaction with Cytoplasmic and Nuclear Components of Epidermal Growth Factor Receptor System." Antioxidants & Redox Signaling, vol. 16, No. 4, pp. 314-328, 2012.

Park, Wh. et al., "A New Matrix Metalloproteinase-9 Inhibitor 3,4-Dihydroxycinnamic Acid (Caffeic Acid) from Methanol Extract of Euonymus Alatus: Isolation and Structure Determination." Toxicology, vol. 207, pp. 383-390, 2005.

Ohgoda, O. et al., "Fibroblast-Migration in a Wound Model of Ascorbic Acid-Supplemented Three-Dimensional Culture System: The Effects of Cytokines and Malotilate, a New Wound Healing Stimulant, on Cell-Migration." Journal of Dermatological Science, vol. 17, pp. 123-131, 1998.

Soobrattee, MA. et al., "Phenolics as Potential Antioxidant Therapeutic Agents: Mechanism and Actions." vol. 579, pp. 200-213, 2005.

Rice- Evans, CA. et al., "Structure—Antioxidant Activity Relationships of Flavonoids and Phenolic Acids." vol. 20, No. 7, pp. 933-956, 1996.

Jan. 28, 2014 International Search Report issued in International Application No. PCT/JP2013/084592.

Sep. 22, 2017 Office Action issued in Chinese Patent Application No. 201380068104.X.

Mar. 16, 2017 combined Office Action and Search Report issued in Chinese Patent Application No. 201380068104.X.

Oct. 25, 2017 Office Action issued in Japanese Patent Application No. 2014-554477.

Cleber A. Schmidt et al., "Structural and Conformational Analysis of Proanthocyanidins from Parapiptadenia rigida and Their Wound-Healing Properties," Journal of Natural Products, vol. 74, pp. 1427-1436, 2011.

L. Pieters et al., "In vivo wound healing activity of Dragon's Blood (Croton spp.), a traditional South American drug, and its constituents," Phytomedicine, vol. 2, No. 1, pp. 17-22, 1995.

\* cited by examiner

WOUND HEALING ACCELERATOR

TECHNICAL FIELD

The present invention relates to use of a specific polyphenol for accelerating wound healing, a wound healing accelerator comprising the same and a pharmaceutical composition for wound healing comprising the same.

BACKGROUND ART

Periodontal disease is an oral disease spreading across the world and one of major causes of tooth loss. Although some active ingredients can be mentioned against such a wound as to include periodontal disease, a demand still exists for compounds capable of accelerating wound healing.

Examples of the compounds that show the accelerating action of wound healing include agents, as an active ingredient, such as an extract from aloes or the like, an antibiotic, an anti-inflammatory agent, kallikrein, adenine, nicotinic acid, allantoin, vitamin A, zinc, a cAMP derivative (Patent Literature 1) and exogenous collagen (Patent Literature 2). In the conventional technique, the improvement of a formulation, etc., to improve the absorbability of such active ingredients had been actively practiced, however, recently, as various findings on the skin histology become clear, attempts to use epidermal growth factor (EGF) for postoperative wound healing have been made (Patent Literature 3).

When an agent is orally administered, a portion of the administered agent acts on the affected area, thereby making it difficult to obtain a sufficient effect and further leaving concern over the manifestation of side effects. Therefore, agents such as an external preparation, which act directly on the skin, are desired for therapy. Few wound healing accelerators, however, are available as an external preparation, and this makes skin wound healing difficult.

At present, as a wound healing accelerator which is commonly used for an external preparation, solcoseryl ointment containing as a main ingredient a calf blood extract, Actosin ointment containing as a main ingredient bucladesine sodium which is a cAMP derivative, and Fiblast spray containing as a main ingredient bFGF (basic fibroblast growth factor), are known. It is, however, required for therapy to apply such an accelerator to the affected area for a long time, and side effects, such as irritation/aching, redness, itching and the increase of exudation, have also been reported. Many of specific polyphenols as disclosed in the present specification, for example, proanthocyanidin and chlorogenic acid which are abundant in grapes and coffee, respectively, abound in familiarity with eating, and can constitute one characteristic feature of being highly safe even upon ingestion. In addition, it takes a certain extent of time for the above drugs to show the effect on fibroblasts, and the action of various growth factors (TGF-β, IL-1α and PDGF) including bFGF that the present inventors had previously tested became detectable on a fibroblast wound model (in vitro) after 24 hours of treatment (Non Patent Literature 1). Thus, any drug or the like to reveal its effect after several minutes of treatment has not been reported.

On the other hand, it has been known that a polyphenol acts as an antioxidant and has a suppressing effect on oxidative damage at inflamed sites in local tissues which are caused by reactive oxygen species produced by inflammatory cells such as neutrophils. A polyphenol is used for an external dermatologic agent, an agent for use in the oral cavity and the like (Patent Literatures 4-9 and Non Patent Literatures 2 and 3). However, it has not been confirmed that any specific polyphenol can accelerate wound healing.

CITATION LIST

Patent Literature

Patent Literature 1
  JP 63-107935 A
Patent Literature 2
  JP 2004-217587 A
Patent Literature 3
  JP 03-106823 A
Patent Literature 4
  International Publication No. WO 2005/092327
Patent Literature 5
  JP 06-336422 A
Patent Literature 6
  Japanese Patent No. 3917370
Patent Literature 7
  Japanese Patent Application No. 2005-213234
Patent Literature 8
  JP 2009-52185 A
Patent Literature 9
  JP 2010-511026 A

Non Patent Literature

Non Patent Literature 1
  O. Ohgoda et al., Journal of Dermatological Science 17 (1998) 123-131.
Non Patent Literature 2
  M. A. Soobrattee et al., Mutation Research 579 (2005) 200-213.
Non Patent Literature 3
  C. A. RICE-EVANS et al., Free Radical Biology & Medicine, Vol. 20, No. 7 (1996) pp. 933-956.

SUMMARY OF INVENTION

Technical Problem

The object of the present invention is to provide a wound healing accelerator effective to accelerate healing of wounds, in particular of intraoral wounds, and pharmaceutical compositions comprising the same. In particular, the invention provides a wound healing accelerator which is expected to work within a short duration of contact and which is easy to handle, and a pharmaceutical composition comprising the same.

Solution to Problem

After an extensive study to achieve the object, the present inventors have found that a specific polyphenol with catechol groups is effective in wound healing, thereby completing the present invention.

Thus, the present invention is as follows.

[1] A pharmaceutical composition for wound healing, comprising at least one of a polyphenol represented by the following general formula:

[Formula 1]

wherein $R_1$-$R_3$ are each independently selected from the group consisting of a hydrogen atom, a halogen atom, a nitro group, a cyano group, a thio group, an alkoxy group, an aryloxy group, a heteroaryloxy group, a carbonyl group, an amino group, a $C_{1-10}$ alkylamino group, a sulfonamide group, an imino group, a sulfonyl group, a sulfinyl group, a $C_{1-10}$ alkyl group, a $C_{3-12}$ cycloalkyl group, a $C_{3-12}$ heterocycloalkyl group, a $C_{9-12}$ bicycloalkyl group, a $C_{3-12}$ heterobicycloalkyl group, a $C_{1-10}$ arylalkyl group, a $C_{1-5}$ heteroarylalkyl group, a $C_{1-10}$ perhaloalkyl group, a $C_{1-3}$ carbonylalkyl group, a $C_{1-3}$ thiocarbonylalkyl group, a $C_{1-3}$ sulfonylalkyl group, a $C_{1-3}$ sulfinylalkyl group, a $C_{1-10}$ aminoalkyl group, a $C_{1-3}$ iminoalkyl group, an aryl group, a heteroaryl group, a $C_{9-12}$ bicycloaryl group and a $C_{4-12}$ heterobicycloaryl group, each of which is substituted or unsubstituted, or any two of $R_1$, $R_2$ and $R_3$ together form a substituted or unsubstituted ring: and X represents a substituted or unsubstituted $C_{1-20}$ aliphatic hydrocarbon group, a substituted or unsubstituted $C_{3-20}$ aromatic hydrocarbon group or a substituted or unsubstituted $C_{3-20}$ polycyclic aromatic hydrocarbon group, a polymer thereof and a pharmaceutically acceptable salt thereof.

[2] The pharmaceutical composition for wound healing according to [1], wherein both $R_2$ and $R_3$ are a hydrogen atom.

[3] The pharmaceutical composition for wound healing according to [1] or [2], wherein $R_1$ is a hydrogen atom.

[4] The pharmaceutical composition for wound healing according to any one of [1]-[3], wherein the polyphenol is selected from the group consisting of caffeic acid, (+)-catechinic acid and chlorogenic acid.

[5] An oral care composition, comprising at least one of a polyphenol represented by the following general formula:

[Formula 2]

wherein $R_1$-$R_3$ are each independently selected from the group consisting of a hydrogen atom, a halogen atom, a nitro group, a cyano group, a thio group, an alkoxy group, an aryloxy group, a heteroaryloxy group, a carbonyl group, an amino group, a $C_{1-10}$ alkylamino group, a sulfonamide group, an imino group, a sulfonyl group, a sulfinyl group, a $C_{1-10}$ alkyl group, a $C_{3-12}$ cycloalkyl group, a $C_{3-12}$ heterocycloalkyl group, a $C_{9-12}$ bicycloalkyl group, a $C_{3-12}$ heterobicycloalkyl group, a $C_{1-10}$ arylalkyl group, a $C_{1-5}$ heteroarylalkyl group, a $C_{1-10}$ perhaloalkyl group, a $C_{1-3}$ carbonylalkyl group, a $C_{1-3}$ thiocarbonylalkyl group, a $C_{1-3}$ sulfonylalkyl group, a $C_{1-3}$ sulfinylalkyl group, a $C_{1-10}$ aminoalkyl group, a $C_{1-3}$ iminoalkyl group, an aryl group, a heteroaryl group, a $C_{9-12}$ bicycloaryl group and a $C_{4-12}$ heterobicycloaryl group, each of which is substituted or unsubstituted, or any two of $R_1$, $R_2$ and $R_3$ together form a substituted or unsubstituted ring: and X represents a substituted or unsubstituted $C_{1-20}$ aliphatic hydrocarbon group, a substituted or unsubstituted $C_{3-29}$ aromatic hydrocarbon group or a substituted or unsubstituted $C_{3-20}$ polycyclic aromatic hydrocarbon group, a polymer thereof and a pharmaceutically acceptable salt thereof.

[6] The oral care composition according to [5], wherein both $R_2$ and $R_3$ are a hydrogen atom.

[7] The oral care composition according to [5] or [6], wherein $R_1$ is a hydrogen atom.

[8] The oral care composition according to any one of [5]-[7], wherein the polyphenol is selected from the group consisting of caffeic acid, (+)-catechinic acid and chlorogenic acid.

[9] The oral care composition according to claims 5 to 8, wherein the composition is in the form of a mouth rinse, a dentifrice, a sweet, a medicament or a film.

[10] A method for accelerating wound healing, comprising the step of contacting a wound with at least one of a polyphenol represented by the following general formula:

[Formula 3]

wherein $R_1$-$R_3$ are each independently selected from the group consisting of a hydrogen atom, a halogen atom, a nitro group, a cyano group, a thio group, an alkoxy group, an aryloxy group, a heteroaryloxy group, a carbonyl group, an amino group, a $C_{1-10}$ alkylamino group, a sulfonamide group, an imino group, a sulfonyl group, a sulfinyl group, a $C_{1-10}$ alkyl group, a $C_{3-12}$ cycloalkyl group, a $C_{3-12}$ heterocycloalkyl group, a $C_{9-12}$ bicycloalkyl group, a $C_{3-12}$ heterobicycloalkyl group, a $C_{1-10}$ arylalkyl group, a $C_{1-5}$ heteroarylalkyl group, a $C_{1-10}$ perhaloalkyl group, a $C_{1-3}$ carbonylalkyl group, a $C_{1-3}$ thiocarbonylalkyl group, a $C_{1-3}$ sulfonylalkyl group, a $C_{1-3}$ sulfinylalkyl group, a $C_{1-10}$ aminoalkyl group, a $C_{1-3}$ iminoalkyl group, an aryl group, a heteroaryl group, a $C_{9-12}$ bicycloaryl group and a $C_{4-12}$ heterobicycloaryl group, each of which is substituted or unsubstituted, or any two of $R_1$, $R_2$ and $R_3$ together form a substituted or unsubstituted ring: and X represents a substituted or unsubstituted $C_{1-20}$ aliphatic hydrocarbon group, a substituted or unsubstituted $C_{3-20}$ aromatic hydrocarbon group or a substituted or unsubstituted $C_{3-20}$ polycyclic aromatic hydrocarbon group, a polymer thereof and a pharmaceutically acceptable salt thereof.

[11] The method according to [10], wherein both $R_2$ and $R_3$ are a hydrogen atom.

[12] The method according to [10] or [11], wherein $R_1$ is a hydrogen atom.

[13] The method according to any one of [10]-[12], wherein the polyphenol is selected from the group consisting of caffeic acid, (+)-catechinic acid and chlorogenic acid.

[14] The method according to any one of [10]-[13], wherein a duration of the contact is 0.01 seconds to 48 hours.

[15] The method according to [14], wherein the duration of the contact is 1 second to 10 minutes.

[16] The method according to any one of [10]-[15], further comprising the step of washing a contact site after the contact.

[17] The method according to any one of claims 10 to 16, wherein the wound is in an oral cavity.

[18] Use of at least one of a polyphenol represented by the following general formula:

[Formula 4]

wherein $R_1$-$R_3$ are each independently selected from the group consisting of a hydrogen atom, a halogen atom, a nitro group, a cyano group, a thio group, an alkoxy group, an aryloxy group, a heteroaryloxy group, a carbonyl group, an amino group, a $C_{1-10}$ alkylamino group, a sulfonamide group, an imino group, a sulfonyl group, a sulfinyl group, a $C_{1-10}$ alkyl group, a $C_{3-12}$ cycloalkyl group, a $C_{3-12}$ heterocycloalkyl group, a $C_{9-12}$ bicycloalkyl group, a $C_{3-12}$ heterobicycloalkyl group, a $C_{1-10}$ arylalkyl group, a $C_{1-5}$ heteroarylalkyl group, a $C_{1-10}$ perhaloalkyl group, a $C_{1-3}$ carbonylalkyl group, a $C_{1-3}$ thiocarbonylalkyl group, a $C_{1-3}$ sulfonylalkyl group, a $C_{1-3}$ sulfinylalkyl group, a $C_{1-10}$ aminoalkyl group, a $C_{1-3}$ iminoalkyl group, an aryl group, a heteroaryl group, a $C_{9-12}$ bicycloaryl group and a $C_{4-12}$ heterobicycloaryl group, each of which is substituted or unsubstituted, or any two of $R_1$, $R_2$ and $R_3$ together form a substituted or unsubstituted ring: and X represents a substituted or unsubstituted $C_{1-20}$ aliphatic hydrocarbon group, a substituted or unsubstituted $C_{3-20}$ aromatic hydrocarbon group or a substituted or unsubstituted $C_{3-20}$ polycyclic aromatic hydrocarbon group, a polymer thereof and a pharmaceutically acceptable salt thereof for manufacturing a wound healing accelerator.

ADVANTAGEOUS EFFECTS OF INVENTION

The wound healing accelerator of the present invention comprising the specific polyphenol is easy to handle and can accelerate wound healing even after a short duration of contact. The accelerator is also expected to have an inhibitory action on oxidative damage at inflamed sites in local tissues, which is caused by reactive oxygen species produced by inflammatory cells such as neutrophils.

DESCRIPTION OF EMBODIMENTS

Details of embodiments according to the present invention are given below.

A wound generally heals through the following steps. First, the wound causes tissue lesion, followed by hemostasis and the inflammatory phase. Subsequently, granulation tissue is formed with vascularization, epidermis regenerates and extends on the resulting granulations, and the healing process proceeds through the wound contraction phase and maturation. During granulation tissue formation (the granulation phase), fibroblasts need to grow. The growth of fibroblasts is observed if they are brought into contact with a specific polyphenol which is effective in accelerating wound healing. Thus, such a polyphenol can accelerate wound healing.

As used herein, "wound" includes abrasions, lacerations, incised wounds and bruises, and also ulcers and burns, which occur on the skin (including the intraoral skin) and other tissues (organs). Wound sites referred to herein are not limited unless explicitly specified, and application can be made on any sites including skin parts of hands, feet, faces, torsos and the like, and intraoral sites, but is preferably on intraoral wounds since the wound healing according to the invention are expected to be effective after even a short duration of contact. Wound healing may also be accelerated in animals other than humans in the same manner.

A polyphenol effective for wound healing is one which has a catechol group (dihydroxyphenyl group) represented by the following general formula:

[Formula 5]

wherein $R_1$-$R_3$ are each independently selected from the group consisting of a hydrogen atom, a halogen atom, a nitro group, a cyano group, a thio group, an alkoxy group, an aryloxy group, a heteroaryloxy group, a carbonyl group, an amino group, a $C_{1-10}$ alkylamino group, a sulfonamide group, an imino group, a sulfonyl group, a sulfinyl group, a $C_{1-10}$ alkyl group, a $C_{3-12}$ cycloalkyl group, a $C_{3-12}$ heterocycloalkyl group, a $C_{9-12}$ bicycloalkyl group, a $C_{3-12}$ heterobicycloalkyl group, a $C_{1-10}$ arylalkyl group, a $C_{1-5}$ heteroarylalkyl group, a $C_{1-10}$ perhaloalkyl group, a $C_{1-3}$ carbonylalkyl group, a $C_{1-3}$ thiocarbonylalkyl group, a $C_{1-3}$ sulfonylalkyl group, a $C_{1-3}$ sulfinylalkyl group, a $C_{1-10}$ aminoalkyl group, a $C_{1-3}$ iminoalkyl group, an aryl group, a heteroaryl group, a $C_{9-12}$ bicycloaryl group and a $C_{4-12}$ heterobicycloaryl group, each of which is substituted or unsubstituted, or any two of $R_1$, $R_2$ and $R_3$ together form a substituted or unsubstituted ring: and X represents a substituted or unsubstituted $C_{1-20}$ aliphatic hydrocarbon group, a substituted or unsubstituted $C_{3-20}$ aromatic hydrocarbon group or a substituted or unsubstituted $C_{3-20}$ polycyclic aromatic hydrocarbon group. Hereinafter, the simplified expression "polyphenol(s) represented by the above general formula" may be used to refer to at least one of the polyphenol represented by the above general formula, a polymer thereof and a pharmaceutically acceptable salt thereof.

Specific examples of the polyphenols represented by the above general formula include caffeic acid, catechins, chlorogenic acid, quercetin, rosmarinic acid, anthocyanidins such as cyanidin, delphinidin, aurantinidin, luteolinidin and petunidin, flavonoids such as cinchonine and quercetin, and polymers thereof. The degrees of polymerization of the polymers are not particularly limited, but polycondensates with the degrees of 2-17 (2-17 mers) are preferable.

Some polyphenols represented by the above general formula are compounds with optical isomerism. All their optical isomers and all the mixtures of the optical isomers are included in the polyphenols represented by the above general formula, and both the racemic mixtures and optical isomers can be used. Optical isomers may be obtained by resolving racemic mixtures through a known method (e.g., preferential crystallization, column chromatography with an optically active stationary phase, and a method that involves conversion of the mixture into diastereomers).

Among the polyphenols represented by the above general formula, caffeic acid, (+)-catechin and chlorogenic acid, and proanthocyanidins, which are polymers of catechins, are preferable. Among proanthocyanidins, oligomers of (+)-catechin, (−)-epicatechin and epicatechingallate are preferable.

Examples of pharmaceutically acceptable salts of the polyphenol represented by the above general formula include Na, K, Li and ammonium salts formed with a phenolic OH; and Na, K, Li and ammonium salts formed with X of the formula (I) in the case where X can form a salt.

Further, crude extracts comprising a compound represented by the above general formula may also be used for the effect of wound healing-accelerating. Examples of the crude extracts include green tea extract, grape seed extract, crimson glory vine extract, blueberry extract and coffee bean extract.

To illustrate methods to obtain the crude extracts, an exemplary case of green tea extract is given below. Green tea extract will be obtained by extracting green tea leaves with water or an organic solvent. In the case of extraction with water, warm or hot water may be used, the purpose of which is to increase the extraction efficiency. Organic solvents, which can be used for the extraction, include those acceptable for manufacture of foods or agents, such as methanol, ethanol and ethyl acetate. Further, supercritical fluid extraction may be performed using liquefied carbon dioxide.

When the above polyphenol is used for accelerating wound healing, in the actual use, a composition comprising the above polyphenol may be used. Such a composition may comprise additives including solvents, which are not particularly limited as long as they do not inhibit the wound healing-accelerating effect of the polyphenol.

Examples of the solvents that can be used for the composition include water, an acidic solution, an alkaline solution and an alcohol solution, and a suitable one may be chosen depending on the location of a wound.

The concentration of the polyphenol in the composition is generally 0.0001-5.0 wt % of the total weight of the composition, but not limited to the range.

Taking into consideration the wound site, as additives in the composition, for example, polishing agents, foaming agents, wetting agent, sweetening agents, flavoring agents, preservatives, various medicinal ingredients, water and ethanol may be suitably added to the composition in the range so as not to interfere with the acceleration of wound healing. The composition may also contain any nutritional supplement as an ingredient, selected from various well-known nutritional supplements such as vitamins, minerals, essential and non-essential amino acids, carbohydrates, lipids, foods and dietary supplements.

Examples of the foaming agents include anionic surfactants, nonionic surfactants, cationic surfactants and amphoteric surfactants.

Examples of the anionic surfactants include salts of acylamino acids such as sodium acylglutamate and sodium acyl sarcosinate, alkylphosphate salts such as sodium alkylphosphate, alkyl sulfate salts, higher fatty acid sulfonated monoglyceride salts, salts of fatty acid esters of isethionic acid, sodium N-methyl-(long-chain acyl)taurates and polyoxyethylene monoalkyl phosphate salts.

Examples of the nonionic surfactants include polyoxyalkylene-adduct surfactants, amine oxide surfactants, mono- or diethanolamide surfactants, sorbitan esters of fatty acids, glycerol esters of fatty acids, polyglycerol esters of fatty acids and sucrose esters of fatty acids.

Examples of the wetting agents include glycerol, sorbitol, polyethylene glycol, propylene glycol, 1,3-butylene glycol, xylitol, maltitol, lactitol and trehalose, which are suitable for use. Erythritol is also suitable for use because of its refreshing and flavoring properties.

Described below are methods of contacting a wound with a wound healing accelerator comprising the polyphenol represented by the above general formula.

In such a contact method, simply contacting the wound site with the wound healing accelerator achieves a wound healing-accelerating effect. Further, the wound healing accelerator can be directly injected. Forms of using a polyphenol represented by the above general formula are not particularly limited, but include solutions, slurries, tablets, powders, capsules, drinkable preparations, ointments and patches. For an intraoral wound, the wound healing accelerator can also be formulated in suitable ways for oral administration by adding them in solutions, dry masses, dentifrices (toothpastes, liquid dentifrices and tooth gels), mouthwashes, mouth rinses, fluid suspensions, topical agents, food supplement powders, pastes, gels, solid foods, sealed foods, wafers, troches, chewing gums, sweets, films and the like.

The duration of contact with the wound site is not particularly limited, but can be short while still achieving a sufficient effect, and is preferably 0.1 seconds-48 hours, more preferably 0.5 seconds-30 minutes, and particularly preferably 1 second-10 minutes.

The wound healing accelerator may be washed away with water or the like to stop its contact with the wound site.

Irradiation of the wound site with an ultraviolet laser at the wavelength of 200-500 nm (preferably 405 nm) during or after the contact still allows the effect of the wound healing accelerator to maintain. The polyphenol can therefore be combined with laser irradiation for the purpose of disinfection. Intraoral use of the wound healing accelerator may also be combined with use of a toothbrush which can irradiate ultraviolet rays having the above wavelength.

EXAMPLES

The following examples illustrate the present invention, but do not limit the invention in any way.

Test 1: Effect of Treating with Proanthocyanidin for One Minute

Cells (mouse-derived 3T3-L1 fibroblasts purchased from DS Pharma Biomedical Co., Ltd. and assayed within five passages), cultured in a 25 cm$^2$ flask under conditions of 37° C. and 5% $CO_2$, were treated with 0.25% Trypsin-EDTA solution (from Life Technologies Corp.), and prepared in medium by the conventional technique to obtain a cell suspension at a concentration of $2\times10^4$ cells/ml. For the culture, 2 ml of glutamine-containing Dulbecco's Modified Eagle Medium (DMEM, Life Technologies Corp., Frederick, Md. USA) supplemented with bovine serum (from Life Technologies Corp.) and penicillin/streptomycin solution (10000 units/ml penicillin and 10 mg/ml streptomycin, from Wako Pure Chemical Industries, Ltd.) at 10% (v/v) and 1% (v/v), respectively, of the total medium was used as the growth medium.

Figure 1:
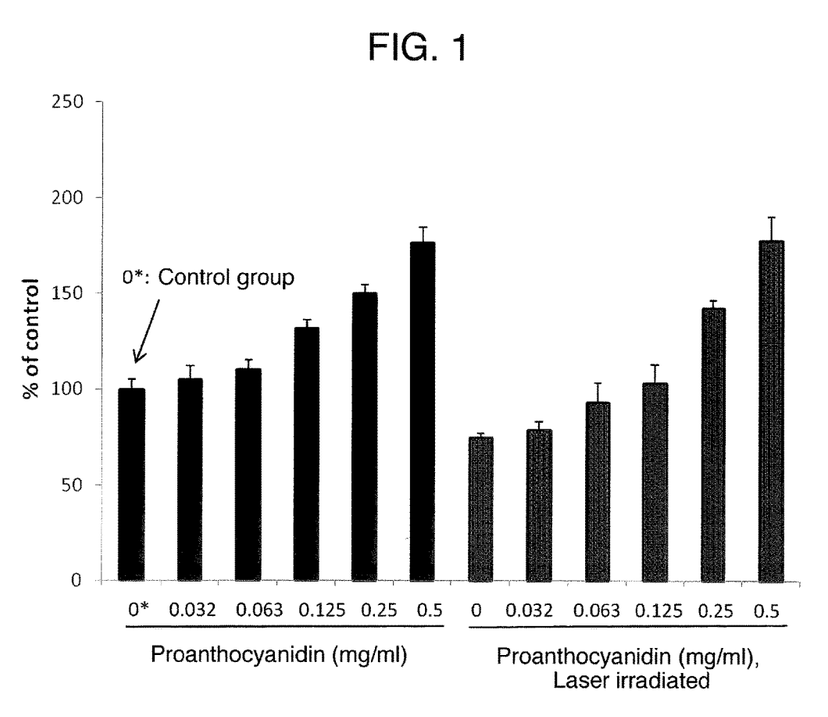
FIG. 1 shows the results of proanthocyanidin treatment and the effect of laser irradiation after the proanthocyanidin treatment.

Each 100 µl aliquot of the cell suspension was plated in each well of a 96-well microplate (from ASAHI GLASS CO., LTD.), which had been coated with type I collagen. After 28-30 hours of culture under conditions of 37° C. and 5% $CO_2$, the medium was removed and 100 µl of proanthocyanidin solution (Leucoselect™, from Indeda Co. Ltd.) was added. One 1 minute later, the proanthocyanidin solution was removed, and the cells were washed with fresh medium. Fresh medium was added again and the cells were further cultured under conditions of 37° C. and 5% $CO_2$. In order to examine the effect of light, another group was prepared from the cells, to which the proanthocyanidin solution had been added, by 405 nm laser irradiation with an output of 300 mW at an irradiation intensity of 930 mW/cm$^2$ for 1 minute (an InGaN semiconductor laser apparatus for experimental use, from RICOH OPTICAL INDUSTRIES CO., LTD.). After the irradiation of this group, the medium was replaced with fresh medium, and the cells were further cultured under conditions of 37° C. and 5% $CO_2$, in the same way as for the other group. After 24 hours of culture, the extent of cell growth was determined by MTT assay. Specifically, after 20 hours of culture, 10 µl of MTT reagent (from Trevigen Inc.) was added to each well and the cells were further cultured for 4 hours under conditions of 37° C. and 5% $CO_2$. After the culture, 100 µl of the Detergent Reagent (Trevigen Inc.) was each added and the cells were left in the dark overnight at room temperature. The absorbance at 595 nm was then determined using a microplate reader (FilterMax™ F5 Multi-Mode Microplate Reader, Molecular Devices, LLC.). Another group, treated with sterile physiological saline, served as the control group, and its absorbance was set at 100% so that the absorbance of each treatment group was calculated as a proportion (%). The results are shown in FIG. 1. The absorbance of the control group in Test 1 was 0.289±0.016.

Test 2: Effect of Treating with Different Polyphenols for One Minute

Figure 2:
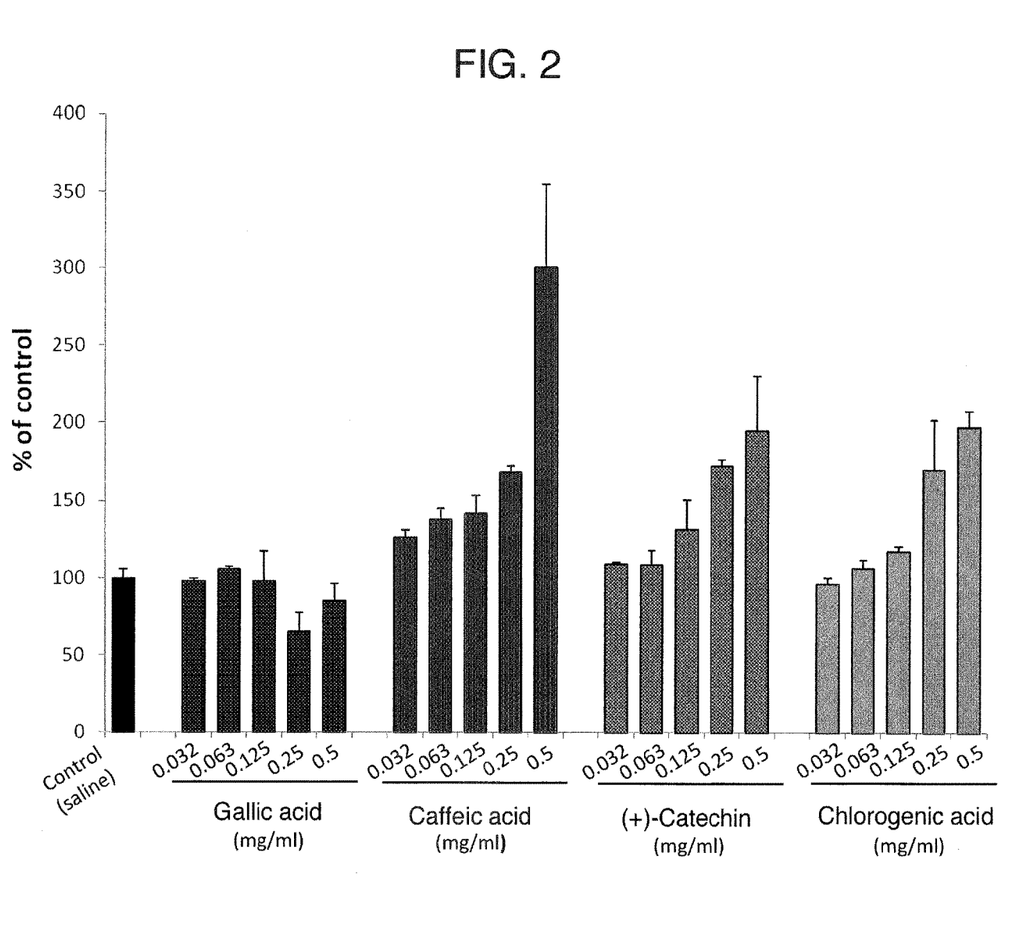
FIG. 2 shows the results of caffeic acid, (+)-catechin and chlorogenic acid treatments.

Gallic acid (from Tokyo Chemical Industry Co., Ltd.), caffeic acid (from Tokyo Chemical Industry Co., Ltd.), (+)-catechin (from Tokyo Chemical Industry Co., Ltd.) and chlorogenic acid (from Sigma-Aldrich Co. LLC.) were assayed. Similarly to the above Test 1, each 100 µl aliquot of the cell suspension was plated in each well of a 96-well microplate, which had been coated with type I collagen. After 27-28 hours of culture under conditions of 37° C. and 5% $CO_2$, the medium was removed and 100 µl of a solution of each test substance was added. One minute later, the solution of the test substance was removed, and the cells were washed with fresh medium. Fresh medium was added again and the cells were further cultured under conditions of 37° C. and 5% $CO_2$. After 24 hours of culture, the extent of cell growth was determined by MTT assay. The results are shown in FIG. 2. The absorbance of the control group in Test 2 was 0.196±0.011.

Figure 3:
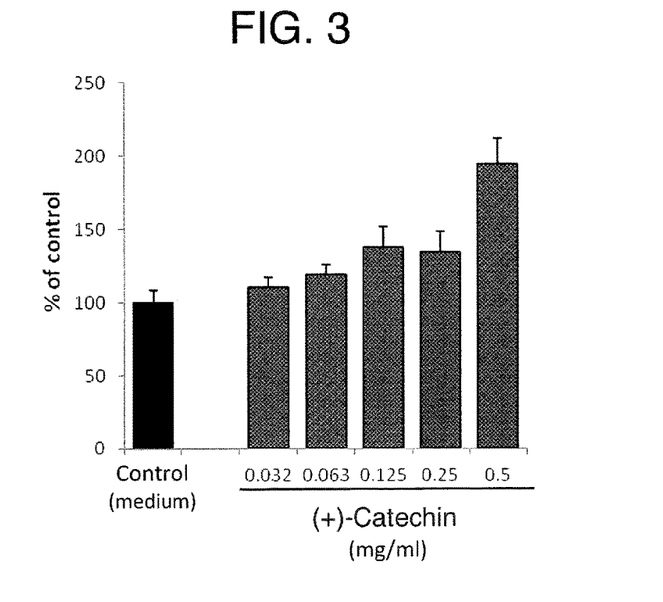
FIG. 3 shows the results of treating with (+)-catechin for 24 hours.

Test 3: Effect of Treating with Catechin for 24 Hours (+)-Catechin was assayed. As in Test 1, each 100 µl aliquot of the cell suspension was plated in each well of a 96-well microplate, which had been coated with type I collagen. After 24 hours of culture under conditions of 37° C. and 5% $CO_2$, the medium was replaced with medium containing the test substance, and the cells were cultured for 24 hours under conditions of 37° C. and 5% $CO_2$. The medium containing the test substance was replaced with fresh medium. 10 µl of MTT reagent (Trevigen Inc.) was added to each well and the cells were further cultured for 4 hours under conditions of 37° C. and 5% $CO_2$. An aliquot (100 µl) of the Detergent Reagent (Trevigen Inc.) was then added and the extent of cell growth was determined as in other Tests. The results are shown in FIG. 3. The absorbance of the control group in Test 3 was 0.163±0.014.

Test 4: Effect of Treating with Green Tea Extract for One Minute

Figure 4:
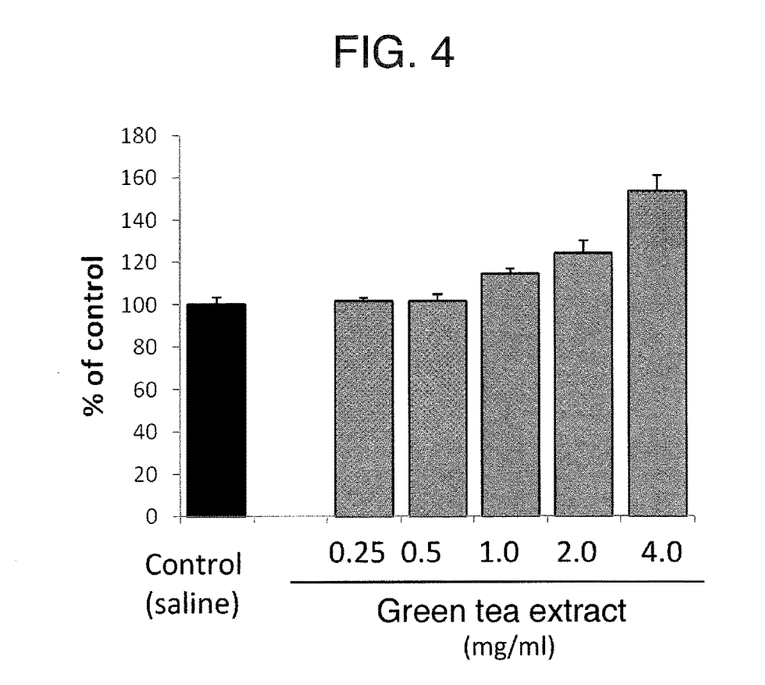
FIG. 4 shows the results of green tea extract treatment.

Green tea extract (from MARUZEN PHARMACEUTICALS CO., LTD.) was assayed. Similarly to the above Test 1, each 100 µl aliquot of the cell suspension was plated in each well of a 96-well microplate, which had been coated with type I collagen. After 28 hours of culture under conditions of 37° C. and 5% $CO_2$, the medium was removed and 100 µl of a solution of the test substance was added. One minute later, the solution of the test substance was removed, and the cells were washed with fresh medium. Fresh medium was added again and the cells were further cultured under conditions of 37° C. and 5% $CO_2$. After 24 hours of culture, the extent of cell growth was determined by MTT assay. The results are shown in FIG. 4. The absorbance of the control group in Test 4 was 0.276±0.010.

Proanthocyanidin, caffeic acid, (+)-catechin, chlorogenic acid and green tea extract used in the tests had been dissolved in physiological saline and sterilized by filtration through a membrane filter (diameter: 0.22 µm).

As can also be seen from the above results, the growth of fibroblasts was observed when the catechol group-containing polyphenols represented by the above general formula were used, and their wound healing-accelerating effect was confirmed. Further, it was also observed that the effect was retained when combined with the use of the laser. The effect on the growth of granulation was also confirmed when the duration of contact was 1 minute-24 hours. On the other hand, no growth of fibroblasts was observed for gallic acid, which is a polyphenol but has a pyrogallol group.

Test 5: Effect of Treating Human Gingival Fibroblasts with Proanthocyanidin for One Minute Cells (human gingival fibroblasts purchased from Primary Cell Co., Ltd. and assayed within five passages), cultured in a 25 cm$^2$ flask under conditions of 37° C. and 5% $CO_2$, were treated with 0.25% Trypsin-EDTA solution (from Life Technologies Corp.), and prepared in medium by conventional technique to obtain a cell suspension at a concentration of $2\times10^4$ cells/ml. For the culture, 2 ml of glutamine-containing Dulbecco's Modified Eagle Medium (DMEM, Life Technologies Corp., Frederick, Md. USA) supplemented with bovine serum (from Life Technologies Corp.) and penicillin/streptomycin solution (10000 units/ml penicillin and 10 mg/ml streptomycin, from Wako Pure Chemical Industries, Ltd.) at 10% (v/v) and 1% (v/v), respectively, of the total medium was used as the growth medium.

Figure 5:
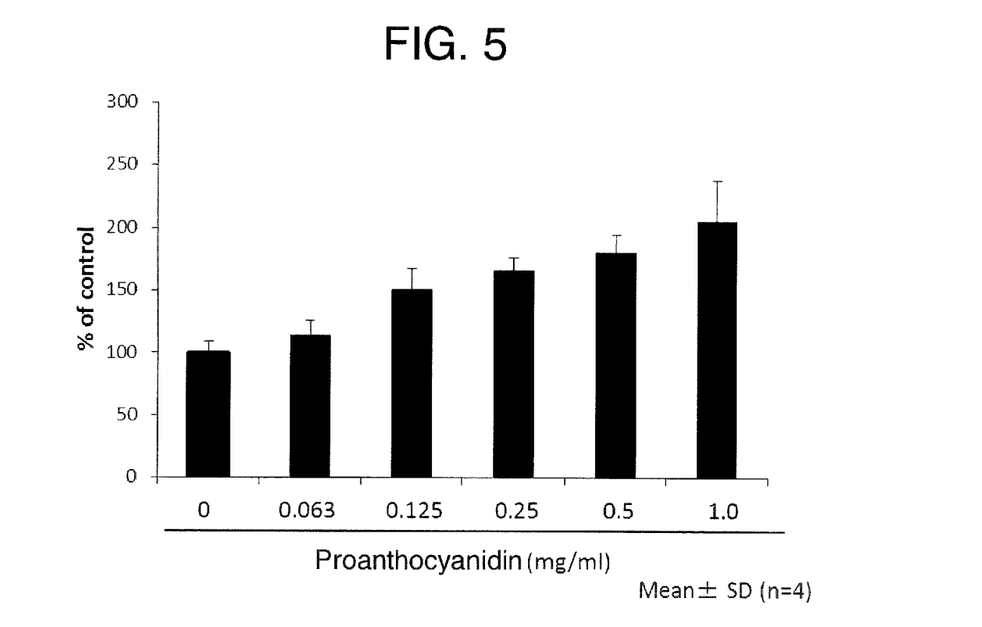
FIG. 5 shows the results of treating human gingival fibroblasts with proanthocyanidin for one minute.

Each 100 µl aliquot of the cell suspension was plated in each well of a 96-well microplate (Corning Corp., N.Y., USA). After 24 hours of culture under conditions of 37° C. and 5% $CO_2$, the medium was removed and 100 µl of a solution of proanthocyanidin (Leucoselect™, from Indeda Co. Ltd.) in sterile physiological saline was added. One minute later, the proanthocyanidin solution was removed, and the cells were washed with fresh medium. Fresh medium was added again and the cells were further cultured under conditions of 37° C. and 5% $CO_2$. After 24 hours of culture, the extent of cell growth was determined by MTT assay. Another group, treated with sterile physiological saline, served as the control group, and its absorbance was set to 100% so that the absorbance of each treatment group was calculated as a proportion (%). The results are shown in FIG. 5. The absorbance of the control group in Test 5 was 0.073±0.007.

Figure 6:
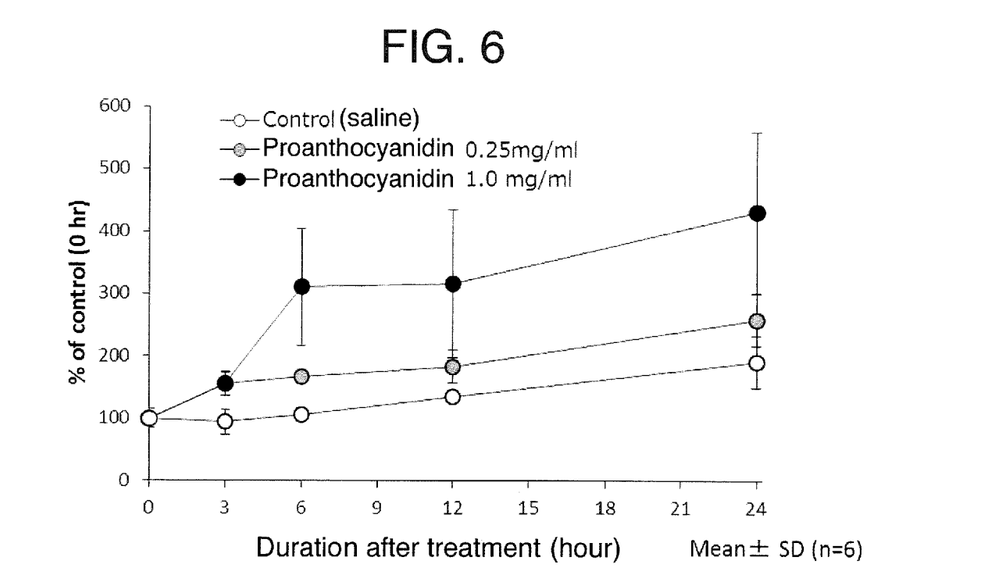
FIG. 6 shows the time-course of growth of proanthocyanidin-treated human gingival fibroblasts.

Test 6: Time-Course of Growth of Proanthocyanidin-Treated Human Gingival Fibroblasts Similarly to the above Test 5, each 100 µl aliquot of the cell suspension was plated in each well of a 96-well microplate. After 24 hours of culture under conditions of 37° C. and 5% $CO_2$, the medium was removed and 100 µl of a solution of 0.25 mg/ml or 1 mg/ml proanthocyanidin in sterile physiological saline was added. One minute later, the proanthocyanidin solution was removed, and the cells were washed with fresh medium. Fresh medium was added again and the cells were further cultured under conditions of 37° C. and 5% $CO_2$. The extent of cell growth was determined by MTT assay over time. The control group was treated with sterile physiological saline in the same way. The results are shown in FIG. 6. The absorbance of the control group at time 0 in Test 6 was 0.088±0.013.

Test 7: Cytoprotective Effect of Proanthocyanidin on Osmotic Stress

Figure 7:
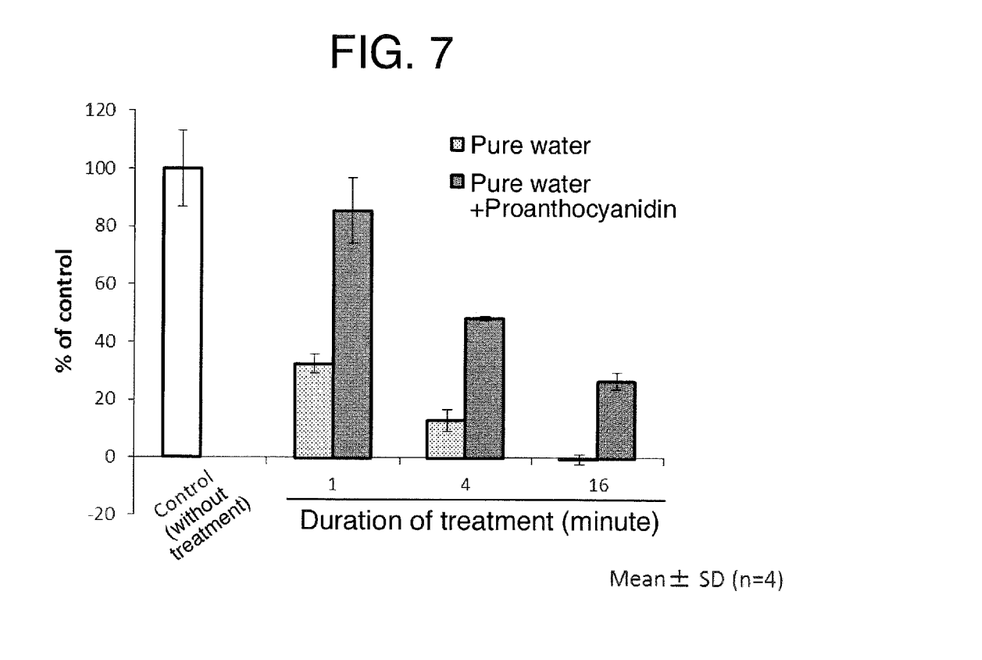
FIG. 7 shows the results of the cytoprotective effect of proanthocyanidin on osmotic stress.

Osmotic stress was applied to cells by exposing them to pure water for defined durations of time, and the effect of proanthocyanidin on the cell were examined. Similarly to the above Test 5, each 100 µl aliquot of the cell suspension was plated in each well of a 96-well microplate. After 15-16 hours of culture under conditions of 37° C. and 5% $CO_2$, the medium was removed and 100 µl of sterile pure water or of a solution of 1 mg/ml proanthocyanidin in sterile pure water was added. One, four or sixteen minutes later, the pure water or the solution of proanthocyanidin in pure water was removed, and the cells were washed with fresh medium. Fresh medium was added again and the cells were further cultured under conditions of 37° C. and 5% $CO_2$. After 24 hours of culture, the extent of cell growth was determined by MTT assay. Another group, cultured for 40 hours without treatment (treated only with medium), served as the control group. The results are shown in FIG. 7. The absorbance of the control group (without treatment) in Test 7 was 0.228±0.030.

Test 8: Cytoprotective Effect of Proanthocyanidin on Starvation Stress

Figure 8:
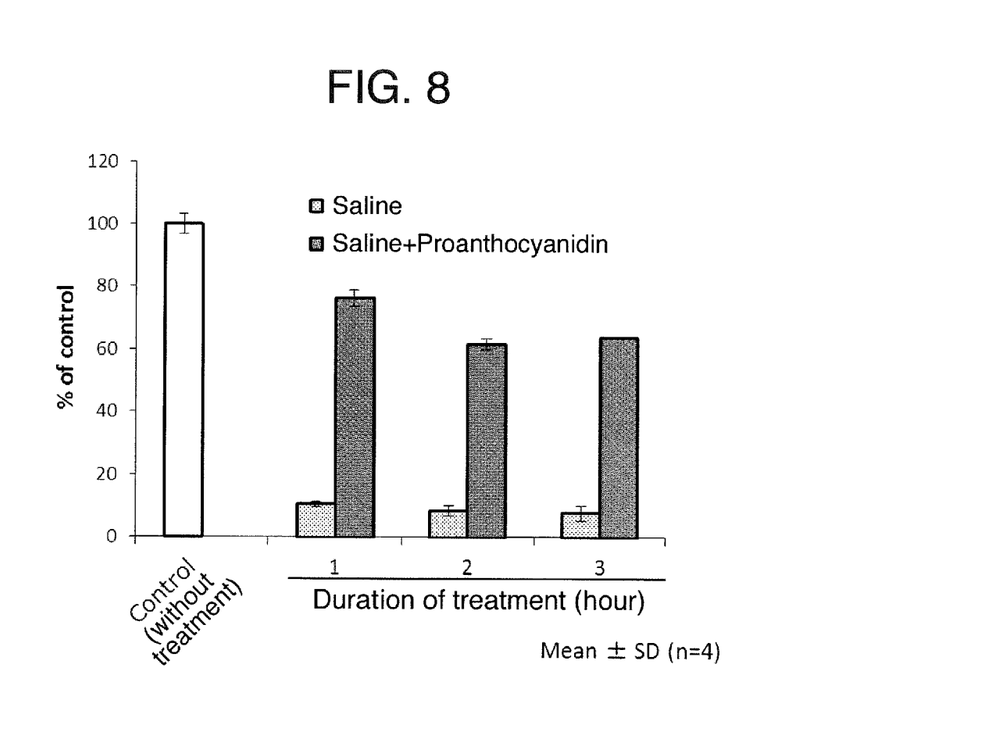
FIG. 8 shows the results of the cytoprotective effect of proanthocyanidin on starvation stress.

Starvation stress was applied to cells by exposing them to sterile physiological saline for 1, 2 and 3 hours, and the effect of proanthocyanidin on the cell were examined. Similarly to the above Test 5, each 100 µl aliquot of the cell suspension was plated in each well of a 96-well microplate. After 19 hours of culture under conditions of 37° C. and 5% $CO_2$, the medium was removed and 100 µl of sterile physiological saline or of a solution of 1 mg/ml proanthocyanidin in sterile physiological saline was added. One, two or three hours later, the sterile physiological saline or the solution of proanthocyanidin in sterile physiological saline was removed, and the cells were washed with fresh medium. Fresh medium was added again and the cells were further cultured under conditions of 37° C. and 5% $CO_2$. After 22-24 hours of culture, the extent of cell growth was determined by MTT assay. Another group, cultured for 44 hours without treatment (treated only with medium), served as the control group. The absorbance of the control group (without treatment) in Test 8 was 0.137±0.004. The results are shown in FIG. 8.

Test 9: Cytoprotective Effect of Proanthocyanidin on Cytotoxicity of Bacterial Endotoxin (Lipopolysaccharide, LPS)

Figure 9:
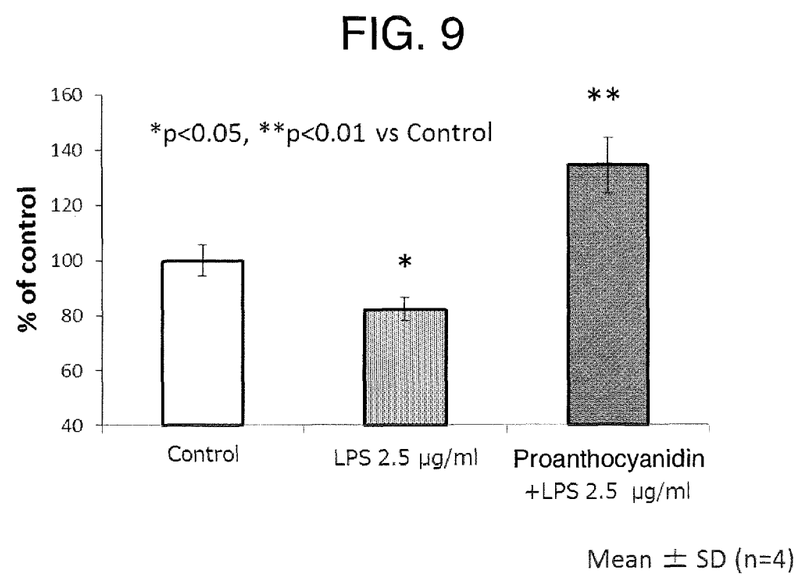
FIG. 9 shows the results of the cytoprotective effect of proanthocyanidin on the cytotoxicity of bacterial endotoxin (lipopolysaccharide, LPS).

Similarly to the above Test 5, each 100 µl aliquot of the cell suspension was plated in each well of a 96-well microplate. After 20 hours of culture under conditions of 37° C. and 5% $CO_2$, the medium was removed and 100 µl of a solution of 1 mg/ml proanthocyanidin in sterile physiological saline was added. The proanthocyanidin solution was removed after 1 minute and the cells were washed with fresh medium. Medium containing *Escherichia coli*—derived lipopolysaccharide (LPS, Wako Pure Chemical Industries, Ltd.) at a concentration of 2.5 µg/ml was added and the cells were further cultured under conditions of 37° C. and 5% $CO_2$. After 24 hours of culture, the extent of cell growth was determined by MTT assay. Another group, cultured for 44 hours without treatment (treated only with medium), served as the control group. The absorbance of the control group in Test 9 was 0.109±0.006. Each sample was analyzed by evaluating the significance of its difference from the mean value of the control group, using Dunnett's multiple comparison test. The results are shown in FIG. 9.

As can be seen from the above results, similarly to mouse fibroblasts, only treating human gingival fibroblasts with proanthocyanidin for one minute also accelerated cell growth in a concentration-dependent manner. Further, the time-course of cell growth shows that the growth was significantly accelerated when compared to the control group at 6 hours after the treatment. Proanthocyanidin, in the test of dissolving it in pure water to evaluate the effect of treatment time, suppressively acted against both the reduction of cell growth by the pure water treatment and of the cells treated by the saline substitution. It was therefore suggested that the polyphenols represented by the above general formula, including proanthocyanidin, also have the cytoprotective effect for fibroblasts, in addition to the growth-accelerating effect therefor. Furthermore, proanthocyanidin not only exerted the protective effect on the cytotoxicity of bacterial endotoxin, but also accelerated cell growth. Thus, it was suggested that proanthocyanidin exerts a wound healing-accelerating effect through the protective and growth-accelerating actions on cells also at the inflammatory damage due to bacterial infection.

INDUSTRIAL APPLICABILITY

The polyphenols represented by the above general formula can, due to their effect, be used as a medical agent, and are therefore useful in medicine, particularly in the fields of skin therapy and therapy in the oral cavity.

The invention claimed is:
1. A method for accelerating healing of intraoral wounds, comprising:
contacting an intraoral wound with proanthocyanidin.
2. The method according to claim 1, wherein a duration of the contact is 0.01 seconds to 48 hours.
3. The method according to claim 2, wherein the duration of the contact is 1 second to 10 minutes.

4. The method according to claim 1, further comprising:
washing a contact site after the contact.
5. The method according to claim 2, further comprising:
washing a contact site after the contact.
6. The method according to claim 3, further comprising:
washing a contact site after the contact.

* * * * *